United States Patent
Beck

(10) Patent No.: US 10,825,169 B2
(45) Date of Patent: *Nov. 3, 2020

(54) METHOD AND APPARATUS FOR FUNCTIONAL MAGNETIC RESONANCE IMAGING

(71) Applicant: Siemens Healthcare GmbH, Erlangen (DE)

(72) Inventor: Thomas Beck, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 113 days.

This patent is subject to a terminal disclaimer.

(21) Appl. No.: 15/983,278

(22) Filed: May 18, 2018

(65) Prior Publication Data

US 2018/0336680 A1 Nov. 22, 2018

(30) Foreign Application Priority Data

May 19, 2017 (DE) .................. 10 2017 208 560

(51) Int. Cl.
| | |
|---|---|
| *G01R 33/48* | (2006.01) |
| *G06T 7/00* | (2017.01) |
| *A61B 5/00* | (2006.01) |
| *A61B 5/055* | (2006.01) |
| *G01R 33/20* | (2006.01) |

(52) U.S. Cl.
CPC .......... *G06T 7/0012* (2013.01); *A61B 5/0042* (2013.01); *A61B 5/055* (2013.01); *G01R 33/20* (2013.01); *G01R 33/4806* (2013.01); *G06T 2207/30016* (2013.01)

(58) Field of Classification Search
CPC .............. G06T 7/00; G06T 7/0012; G06T 2207/30016; G01R 33/20; G01R 33/48; G01R 33/4806; A61B 5/055; A61B 5/00; A61B 5/0042
See application file for complete search history.

(56) References Cited

U.S. PATENT DOCUMENTS

2013/0123607 A1* 5/2013 Leuthardt ............ A61B 5/0042
  600/410
2018/0333068 A1 11/2018 Beck

OTHER PUBLICATIONS

Khullar et al., "Wavelet-based fMRI analysis: 3-D denoising, signal separation, and validation metrics," Neuroimage, vol. 54, No. 4, pp. 2867-2884 (2011).
Krizhevsky et al., "ImageNet Classification with Deep Convolutional Neural Networks," Advances in Neural Information Processing Systems, pp. 1-9 (2012).

(Continued)

*Primary Examiner* — Son T Le
(74) *Attorney, Agent, or Firm* — Schiff Hardin LLP

(57) ABSTRACT

An ICA to identify a large number of candidate correlation patterns is carried out based on a time series of image data. The large number of candidate correlation patterns includes a large number of neurophysical events, as well as false patterns owing to noise. The neurophysical events as well as the false patterns are then separated, for example on the basis of a metric, which indicates an intensity of the candidate correlation patterns in a section of the brain, or by a computer-implemented classifier. Techniques of this kind can be used in conjunction with functional magnetic resonance imaging.

11 Claims, 4 Drawing Sheets

(56) References Cited

OTHER PUBLICATIONS

Lawrence et al., "Face Recognition: A Convolutional Neural-Network Approach," IEEE Transactions on Neural Networks, vol. 8, No. 1, pp. 98-113 (1997).

Rumelhart et al., "Learning representations by back-propogating errors," Nature, vol. 323, No. 9, pp. 533-536 (1986).

Van Den Heuvel et al., "Exploring the brain network: A review on resting-state fMRI functional connectivity," European Neuropsychopharmacology, vol. 20, pp. 519-534 (2010).

Beckmann et al., "Investigations into resting-state connectivity using independent component analysis," Phil. Trans. R. Soc. B, vol. 360, pp. 1001-1013 (2005).

Greicius et al., "Regional Analysis of Hippocampal Activation During Memory Encoding and Retrieval: fMRI Study," Hippocampus, vol. 13, pp. 164-174 (2003).

Salimi-Khorshidi et al., "Automatic Denoising of Functional MRI Data: Combining Independent Component Analysis and Hierarchical Fusion of Classifiers," Neuroimage, vol. 90, pp. 449-468 (2014).

Greicius et al., "Functional connectivity in the resting brain: A Network analysis of the default mode hypothesis," PNAS, vol. 100, No. 1, pp. 253-258 (2003).

Setsompop et al., "Blipped-Controlled Aliasing in Parallel Imaging (blipped-CAIPI) for simultaneous multi-slice EPI with reduced g-factor penalty," Magn. Reson. Med., vol. 67, No. 5, pp. 1210-1224 (2012).

Breuer et al., "Controlled Aliasing in Parallel Imaging Results in Higher Acceleration (CAIPIRINHA) for Multi-Slice Imaging," Magnetic Resonance in Medicine, vol. 53, pp. 684-691 (2005).

Thesen et al., "Prospective Acquisition Correction for Head Motion With Image-Based Tracking for Real-Time fMRI," Magnetic Resonance in Medicine, vol. 44, pp. 457-465 (2000).

Griswold et al., "Generalized Autocalibrating Partially Parallel Acquisitions (GRAPPA)," Magnetic Resonance in Medicine, vol. 47, pp. 1202-1210 (2002).

Souza et al., "SIMA: Simultaneous Multislice Acquisition of MR Images by Hadamard-Encoded Excitation," Journal of Computer Assisted Tomography, vol. 12, No. 6, pp. 1026-1030 (1988).

Larkman et al., "Use of Multicoil Arrays for Separation of Signal from Multiple Slices Simultaneously Excited," Journal of Magnetic Resonance Imaging, vol. 13, pp. 313-317 (2001).

\* cited by examiner

METHOD AND APPARATUS FOR FUNCTIONAL MAGNETIC RESONANCE IMAGING

BACKGROUND OF THE INVENTION

Field of the Invention

The invention relates to techniques for evaluating image data of functional magnetic resonance imaging, in particular, to techniques for separating correlation patterns of neurophysical events and false patterns during the course of an independent component analysis.

Description of the Prior Art

Magnetic resonance imaging (MRI) can be used to analyze neurophysical events. In particular, MRI can be used to analyze functionally correlated regions of the brain (anatomical neural networks) in relation to neurophysical events. The anatomical neural networks can be made visible by identification of correlation patterns of the neurophysical events. The correlation patterns can denote a temporal and/or spatial correlation of neurophysical events.

One appropriate technique for this purpose is functional MRI (fMRI). With fMRI, temporal changes in image contrast are displayed by suitable MR imaging scanning sequences. For example, contrast that is dependent on the blood oxygen level can be examined during the course of fMRI, also called BOLD contrast (blood oxygenation level dependent). Neurophysical events can be scanned as a result.

One special technique of fMRI is known as resting-state fMRI (rsfMRI). With rsfMRI, the time dependency between neurophysical events separated in space (functional connectivity) is taken into account, wherein no or no significant external stimuli are specified to the anatomical neural network. For example, with rsfMRI, the examination patient is not allowed to perform particular activities or thoughts (resting state).

With rsfMRI, an extensive time series of three-dimensional image data is analyzed in order to examine the functionality and correlations of the brain activity in the resting state. A particularly high time resolution can be achieved by accelerated imaging sequences. For example, a number of two-dimensional slices can be simultaneously excited and read out in an examination region of an examination patient. See, for example, Souza, S. P., et al. "SIMA: simultaneous multislice acquisition of MR images by Hadamard-encoded excitation." Journal of computer assisted tomography 12.6 (1988): 1026-1030; and Setsompop, Kawin, et al. "Blipped-controlled aliasing in parallel imaging for simultaneous multislice echo planar imaging with reduced g-factor penalty." Magnetic Resonance in Medicine 67.5 (2012): 1210-1224; and Breuer, Felix A., et al. "Controlled aliasing in parallel imaging results in higher acceleration (CAIPIRINHA) for multi-slice imaging." Magnetic resonance in medicine 53.3 (2005): 684-691.

The quantity of MR data increases as a result of the higher time resolution. As the quantity of data to be analyzed increases, so does the computationally-intensive preprocessing of the image data use considerably more time. Typical time series have a period of about 6-8 minutes and can depict, for example, 700-1000 volume regions, each having 70-80 slices.

With rsfMRI, different techniques are used for evaluating the time series of image data. Evaluation is based on an independent component analysis (ICA). The ICA is conventionally based on model assumptions as a function of the current data set, such as seed points, which a priori control the evaluation or descriptions of an external stimulus. This means that the correlation patterns can be identified without an a priori limitation. With ICA, correlation patterns are sought in the underlying image data, which can explain the changes in intensity in the time series of image data as a consequence of neurofunctional events. Mutually independent candidate correlation patterns are detected by the ICA. These are also called components of the ICA. The large number of candidate correlation patterns includes correlation patterns of the large number of neurophysical events, as well as false patterns, which are obtained, for example, due to noise in the image data or inevitably from the algorithm of the ICA that is used. The false patterns are often of subordinate interest and should be screened out.

With conventional techniques of rsfMRI it can be laborious to bring about a separation between the correlation patterns of the neurophysical events and the false patterns. For example, it can be necessary to manually classify a large number of candidate correlation patterns, which are identified by the ICA, as a relevant correlation pattern of the neurophysical events or as false patterns. This can be time-consuming and prone to errors.

Therefore, there is a need for improved techniques of MRI of neurophysical events in the brain of an examination person. In particular, there is a need for rsfMRI techniques, which eliminate or alleviate at least some of the drawbacks and limitations mentioned above.

SUMMARY OF THE INVENTION

In the fMRI method according to the invention, a time series of image data is obtained. The time series of image data depicts a large number of neurophysical events in the brain of an examination person in a spatially resolved manner. The time series is provided to a computer and the method also includes carrying out an ICA in the computer so as to identify a large number of candidate correlation patterns based on the time series of image data. The large number of candidate correlation patterns includes correlation patterns of the large number of neurophysical events as well as false patterns, for example due to noise or changes in intensity caused by other effects, such as physiological effects—for example heartbeat or breathing—or heating of the scanner. The method also includes determining, in the computer, a section of the brain. The method also comprises for each candidate correlation pattern from the large number of candidate correlation patterns: determining a corresponding value of a predefined metric. The metric indicates an intensity of the respective candidate correlation pattern in the section. The method also includes choosing at least one candidate correlation pattern from the large number of candidate correlation patterns based on the determined values of the predefined metric. The method also includes marking the chosen at least one candidate correlation pattern for analysis by a user at a display in communication with the computer.

The present invention also encompasses a non-transitory, computer-readable data storage medium encoded with programming instructions that, when the storage medium is loaded into a computer or computer system of a magnetic resonance apparatus, cause the computer or computer system to implement any or all embodiments of the method according to the invention, as described above.

The present invention also encompasses a magnetic resonance apparatus having a computer or computer system that is configured to operate the magnetic resonance apparatus so as to implement any or all of the embodiments of the method according to the invention, as described above.

Use of ANNs to identify correlation patterns of neurophysical events of a neural network in a large number of candidate correlation patterns is disclosed.

DESCRIPTION OF THE PREFERRED EMBODIMENTS

Figure 1:
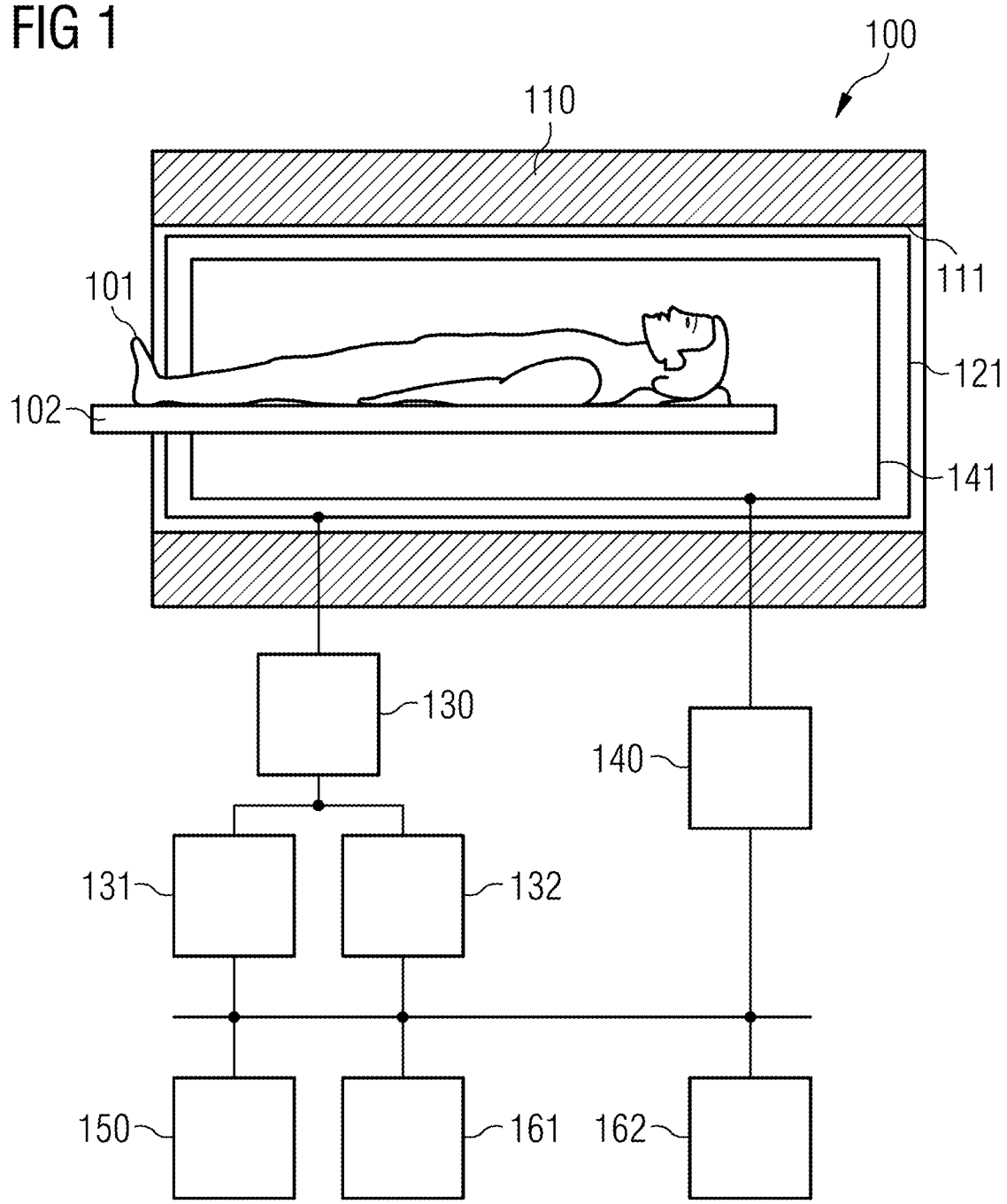
FIG. 1 schematically illustrates an MR system that can be used for the inventive techniques of rsfMRI.

The present invention will be described in more detail below using preferred embodiments with reference to the drawings. In the figures, identical reference numerals designate identical or similar elements. The figures are schematic representations of different embodiments of the invention. Elements illustrated in the figures are not necessarily shown true to scale. Instead, the various elements illustrated in the figures are reproduced in such a way that their function and general purpose is clear to a person skilled in the art. Connections and couplings between functional units and elements illustrated in the figures can also be implemented as an indirect connection or coupling. A connection or coupling can be wired or wireless. Functional units can be implemented as hardware, software or a combination of hardware and software.

Techniques will be described below to render the functional connectivity of a neural network, such as for example of the brain of an examination person, visible. In other words, this means that techniques will be described below to identify neurophysical events in the brain of an examination person as well as associated correlation patterns. The techniques described here enable the neurophysical events and the associated correlation patterns in the brain of the examination person to be identified automatically and particularly reliably. In particular, by means of the techniques described herein it can be unnecessary for an operator, such as, for example medical staff, to manually annotate a large number of candidate correlation patterns, which comprises the correlation patterns of the large number of neurophysical events, but also false patterns for example owing to noise, in order to separate the false patterns from the correlation patterns of the neurophysical events.

In various techniques described herein a time series of image data is obtained, which depicts the neural network three-dimensionally using a suitable contrast. For example, the image data can be MR image data having BOLD contrast. For example, a corresponding MR scanning sequence could be carried out in the various techniques described herein, which acquires the time series of image data. For example, it would be possible for the MR scanning sequence to be image-accelerated, for example uses SMS techniques or undersampling of the spatial frequency range. As a result, a particularly high time resolution can be obtained, so the time series of image data has a particularly large number of time steps. Alternatively, an increased spatial resolution or a mixture of increased spatial and temporal resolution can also be achieved due to the acceleration of the scanning sequence.

An ICA can then be carried out in the various techniques described herein, based on the time series of image data. For example, in the various techniques described herein it may be unnecessary to define a seed point in relation to a section of the examination region or the neural network before the ICA is performed. By means of the ICA a large number of candidate correlation patterns is obtained, which comprise the actual correlation patterns of the neurophysical events—which depict the functional connectivity of the neural network—as well as false patterns, for example owing to noise, signal changes for example due to the scanner heating up, particular properties of the algorithm underlying the ICA and/or for instance also changes in intensity caused by physiological effects such as breathing or heartbeat. According to various techniques it is possible to carry out targeted separation of the correlation patterns of the neurophysical events from the false patterns. In particular, in the various techniques described herein it is possible to carry out this separation completely automatically or largely automatically. For example, by means of the techniques described herein it may be unnecessary for medical operators to manually classify the quantity of candidate correlation patterns.

For this purpose, a section of the brain, or in general of the neural network, is determined manually, semi-automatically or completely automatically in various examples. A one-dimensional or multi-dimensional value of a predefined metric is then determined for each candidate correlation pattern, which is obtained from the ICA. The metric can indicate an intensity of the respective candidate correlation pattern in the section. It is then possible to choose one or more candidate correlation pattern(s) from the large number of candidate correlation patterns based on the determined values of the predefined metric. For example, threshold value comparisons could be carried out with a predefined threshold value. The candidate correlation patterns, which have a particularly high intensity in the chosen section, for example compared with other candidate correlation patterns or compared with an absolute reference, can then be chosen and marked for analysis by a user.

By means of the section it is possible to limit the sample space of the ICA—which corresponds to the large number of candidate correlation patterns—to those candidate correlation patterns, which have a significant intensity in the section. For example, the section can correspond to an examination region (Region of Interest, ROI), which is to be analyzed in more detail for diagnosis. Due to the reduction in the size of the sample space of the ICA, the candidate correlation patterns to be checked by the user can be greatly reduced. For example, it would be possible for the number of candidate correlation patterns chosen on the basis of the metric to not be greater than 10%, optionally not greater than 5%, more optionally not greater than 1%, with respect to the total number of candidate correlation patterns.

In some examples, by appropriate choice of the metric, it can also be possible that when choosing the candidate correlation patterns based on the determined values of the predefined metric, false patterns and correlation patterns of the neurophysical events can be separated at the same time. In other words, this means that by appropriate choice of the metric, it may also be possible to choose, with a particularly high degree of probability, only correlation patterns of the neurophysical events and to achieve a separation between correlation patterns of the neurophysical events and false patterns in this way.

In techniques of this kind, in contrast to reference implementations, the section is not taken into account during the course of implementation of the ICA. The section can only be taken into account after implementation of the ICA. This means that the evaluation of the time series of image data is carried out without an a priori model assumption relating to a seed region.

A further example of evaluation of the large number of candidate correlation patterns is based on the use of a suitably trained computer-implemented classifier. The classifier can achieve a separation of the false patterns and the correlation patterns of the large number of neurophysical events. For example, an artificial neural network (ANN), such as, for instance an artificial Convolutional Neural Network (CNN) could be used.

For example, the ANN can have a number of layers. For example, the ANN can comprise an input layer, a plurality of hidden layers and an output layer. The input layer can comprise a quantity of neurons, wherein the number of neurons corresponds to the number of image points of a candidate correlation pattern—or a component identified by the ICA. The various candidate correlation patterns can then each be transferred as input values (input feature map) to the input layer. The input layer can be connected by a plurality of hidden layers to the output layer. A corresponding neuron can exist in the output layer for each category to be classified, which neuron provides as an output value the affiliation of the respectively transferred candidate correlation pattern to the respective category (output feature map).

Different types of separation can occur in the various examples described herein. For example, in a simple implementation, the output layer can comprise two neurons, one for the correlation patterns of the neurophysical events and one for the false patterns. A distinction could also be made between more than just two categories, however. For example, the classifier could also be adapted for separation between correlation patterns of neurophysical events caused by physiological events and correlation patterns of spontaneous neurophysical events. This means that a distinction can be made between neurophysical events caused for example by heartbeat or breathing and associated correlation patterns and other neurophysical events and associated correlation patterns by means of the classifier.

It would also be possible for the classifier to also be adapted for separation between correlation patterns of different types of spontaneous neurophysical events. For example, the correlation patterns of the different spontaneous neurophysical events could be classified according to which regions of the brain have a particularly high corresponding intensity.

FIG. 1 schematically illustrates an MR system 100, which can be used for carrying out the above-described techniques and the techniques which are described below. The MR system 100 has a scanner 110, which defines a tube 111. The scanner 110 has a basic field magnet that generates a basic magnetic field parallel to its longitudinal axis.

An examination object, here an examination patient 101, can be moved on a bed 102 into the scanner 110. An examination region of the examination patient 101 can be taken into account during MR imaging. In the example of FIG. 1, the head of the examination patient 101, in particular in the region of the brain. The brain forms a neural network, and neurophysical events of the brain are to be rendered visible.

The MR scanner 110 also has a gradient system 140 for generating gradient fields, which spatially encode the acquired MR data. Typically, the gradient system 140 has at least three separately controllable gradient coils 141 that are positioned so as to be well defined from each other. The gradient coils 141 enable gradient pulses to be activated along particular spatial directions (gradient axes), which pulses generate the gradient fields. These gradient axes define a machine coordinate system. The gradient fields can be used, for example, for slice selection, for frequency encoding (in the readout direction) and for phase encoding. Spatial encoding of the MR data is achieved as a result.

An RF coil arrangement 121 is provided that radiates an amplitude-modulated or frequency-modulated RF excitation pulse into the examination patient 101. A transverse magnetization of certain nuclear spins in the patient 101 is produced as a result. An RF transmitting system 131 is connected by an RF switch 130 to the RF coil arrangement 121 in order to generate such RF excitation pulses. The RF transmitting system 131 can include an RF generator and an RF amplitude modulation unit. The RF excitation pulses tilt the transverse magnetization 1D slice-selectively or 2D/3D location-selectively or globally from the resting position. Alternatively or in addition to the RF excitation pulses, RF refocusing pulses can be radiated. The transverse magnetization can then be simultaneously modified in a number of slices, for example in SMS scanning sequences.

Furthermore, an RF receiving system 132 is coupled via the RF switch 130 to the RF coil arrangement 121. MR signals of the relaxing transverse magnetization, for example due to inductive coupling into the RF coil arrangement 121, can be acquired or scanned as MR data with the RF receiving system 132. MR data can be simultaneously obtained from more than one slice in the SMS scanning sequence.

The MR data are initially in the form of raw data in the spatial frequency domain. When using image-accelerated MR scanning sequences, undersampling in the spatial frequency domain can exist. In such cases it can be necessary to optionally reconstruct or complete the MR data and then transform it into the image domain in order to obtain image data. A processor 161 of the MR system 100 performs these functions.

The MR system 100 also has an operating console 150, which can include for example, a screen, a keyboard, a mouse, etc. User inputs can be detected and outputs to the user can be implemented via the operating console 150. For example, it can be possible to adjust individual operating modes or operating parameters of the MR system 100 by the user and/or automatically and/or remote-controlled via the operating console 150.

The processor 161 can be a processor, a microprocessor or a microcontroller. The processor 161 can alternatively be a field-programmable array (FPGA) or an application-specific integrated circuit (ASIC). The MR system 100 also has a memory 162. Control instructions can be stored in the memory 162. The control instructions are executed by the processor 161. Execution of the control instructions by the processor 161 cause the processor 161 to execute various techniques so as to determine a scanning sequence on the basis of which the acquires raw data are entered as numerical data in k-space, according to the gradients that are activated by the gradient system 140.

Execution of the control instructions by the processor 161 causes the processor 161 to execute techniques for SMS imaging, and for post-processing of a time series of image data in connection with rsfMRI. For example, the processor 161 can implement an ICA so as to identify a large number of candidate correlation patterns, which comprise correlation patterns of neurophysical events as well as false patterns. The processor 161 can then carry out techniques in order to separate the false patterns from the correlation patterns of the neurophysical events from the components or candidate correlation patterns identified by the ICA. For this purpose, the processor 161 can apply a computer-implemented classifier and/or metric, which indicates an intensity of the various candidate correlation patterns in a section of the brain.

Figure 2:
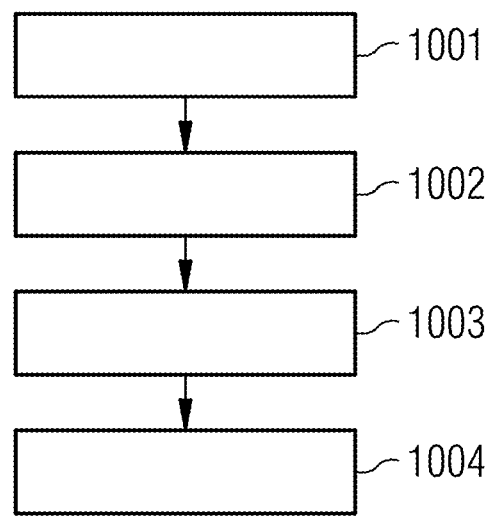
FIG. 2 is a flowchart of an example of the method according to the invention.

FIG. 2 is a flowchart of an exemplary method. The method of FIG. 2 could be carried out by the processor 161.

First, in step 1001, a time series of image data is obtained. For example, an MR scanning sequence could be carried out in step 1001 in order to obtain raw data using BOLD contrast. For example, the MR scanning sequence could comprise SMS imaging with undersampling of the spatial frequency range, and simultaneous excitation and reading of a number of slices. For example, undersampled raw data could be reconstructed in step 1001, for example using techniques of partially parallel acquisition, such as Grappa Griswold, Mark A., et al. "Generalized autocalibrating partially parallel acquisitions (GRAPPA)." Magnetic resonance in medicine 47.6 (2002): 1202-1210.

Various preprocessing steps can optionally occur in step 1002.

For example, it is possible for a movement of the examination person to be compensated during the course of preprocessing. For example, a compensation could occur in the sub-voxel range. For example, a rigid movement correction could be carried out. See for example Thesen, Stefan, et al. "Prospective acquisition correction for head motion with image-based tracking for real-time fMRI." Magnetic Resonance in Medicine 44.3 (2000): 457-465.

A further aspect of corresponding preprocessing can relate for example to a normalization of the contrast in the image data. Temporal drifts in the amplitude of the contrast can be compensated in this way.

A further technique, which can be taken into account in connection with preprocessing the image data, relates to filtering of the course over time of the contrast, for example for individual voxels of the image data. For example, temporal bandpass filtering could be carried out. Typically, a frequency of the observed signal changes lies in a specific frequency band, for example in the region of 8 mHz to 150 mHz in connection with rsfMRI. See for example Greicius, Michael D., et al. "Regional analysis of hippocampal activation during memory encoding and retrieval: fMRI study." Hippocampus 13.1 (2003): 164-174.

A further technique, which can be taken into account in connection with the pre-processing in step 1001, relates to spatial filtering. For example, a Gaussian kernel with a full width at half maximum of 3-4 mm could be applied. Signal artifacts can be reduced in this way.

A temporal correction of the image data, which depict different slices inside the brain, can be performed during the course of pre-processing. For example, the type of time offset between acquisition of MR data in different slices can be compensated.

The examples of techniques illustrated above, which were described in the context of pre-processing step 1002, are exemplary techniques. In other examples it would be possible to apply only some of the techniques described above or else to apply other techniques for pre-processing the image data in step 1002.

The ICA is then carried out in step 1003. A large number of candidate correlation patterns is identified on the basis of the ICA. The candidate correlation patterns correspond to independent components, which are identified by the ICA. The time series of image data can be described by overlaying the independent components. Each candidate correlation patterns can for example indicate a particular intensity in different voxels of the image data. Each candidate correlation pattern can for example be associated with a particular time dependency of an underlying signal path. Basically, different voxels, which contribute to a candidate correlation pattern, can have identical or complementary signal paths or ones that are phase shifted in relation to each other in some other way.

For example, the signal path of the various voxels of the time series of image data can be described as a linear combination of different components during the course of the ICA. Each instant can correspond for example to an observation. The number of instants can therefore denote the number of observations, which is generated from a particular other number of components. In other words, the ICA can be adapted to identify a mixture of underlying components, which describe the scanned image data.

The ICA provides components, which have a maximum independence from each other. The ICA can be applied to the entire scanning region so as to be resolved for different voxels. Details of the ICA in connection with resting state fMRI are described for example in: Beckmann, Christian F., et al. "Investigations into resting-state connectivity using independent component analysis". Philosophical Transactions of the Royal Society of London B: Biological Sciences 360.1457 (2005): 1001-1013. The number of actual sources, in other words, the correlation patterns of actual neurophysical events, is not necessarily equal to the number of candidate correlation patterns, which are identified as components during the course of the ICA.

For this reason, false patterns and correlation patterns of the neurophysical events are separated in step 1004 based on the large number of candidate correlation patterns identified by the ICA.

Figure 3:
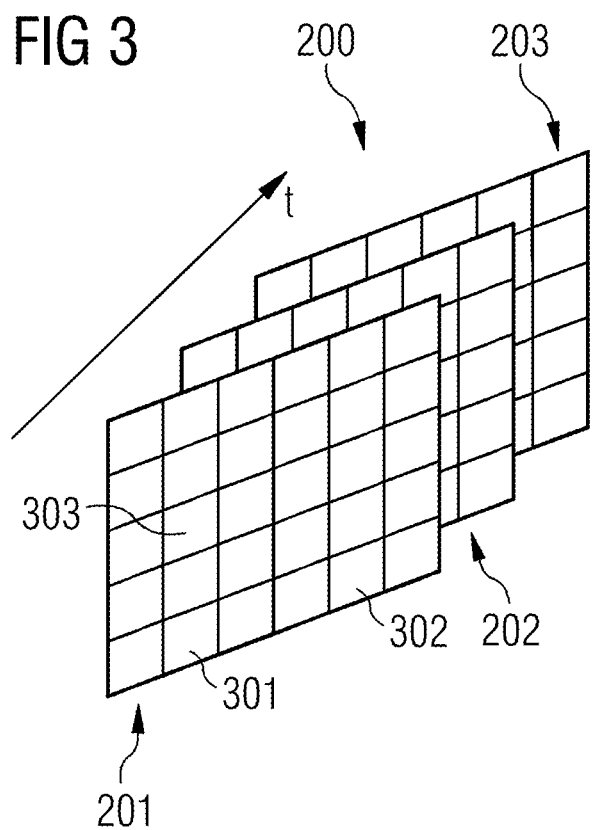
FIG. 3 illustrates a time series of image data, which can be obtained according to various examples by an MR image sequence with BOLD contrast.

FIG. 3 illustrates aspects in relation to a time series 200 of image data 201-203. FIG. 3 illustrates that different image data 201-203 is obtained at different instants. FIG. 3 illustrates an example in which in each case two-dimensional image data 201-203 of a particular slice of an examination region is obtained at different instants. In other examples it would also be possible, however, for in each case three-dimensional image data 201-203 to be obtained per instant, which depicts a three-dimensional examination region, for example the brain of an examination person.

Each image point of the image data can have a contrast, which corresponds to a signal integrated in a voxel of the examination region. The contrast can be for example a BOLD contrast.

The image data 201-203 can be obtained for example with an MR scanning sequence. The image data 201-203 can for example be suitably pre-processed, for example in step 1002 of the method in FIG. 2.

Three image points 301-303 are also highlighted in FIG. 3.

Figure 4:
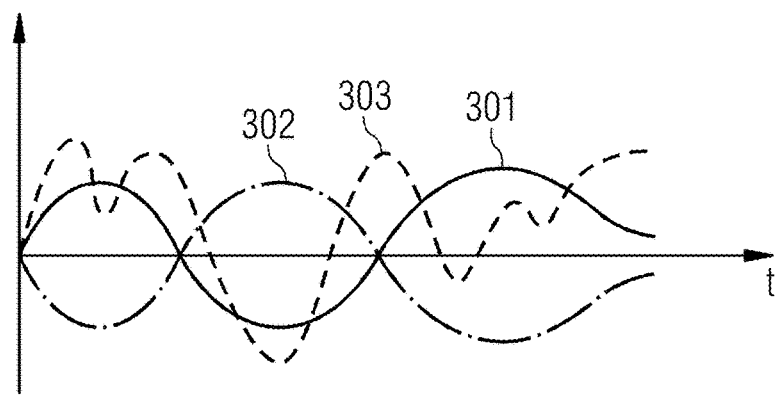
FIG. 4 schematically illustrates a course of time of the contrast in different voxels of the image data according to the invention.

FIG. 4 illustrates aspects in relation to a temporal signal path of the contrast in the image points 301-303. It can be seen from FIG. 4 that the contrast in the image points 301-303 varies as a function of time. The number of instants for which the contrast is available in the various image points is sometimes also called the number of observations. Each instant can therefore represent an observation. With accelerated imaging, the time resolution, and therewith the number of observations, can be particularly high.

In FIG. 4, for example the contrast in the image point 301 has a high correlation with the signal path of the contrast in the image point 302. This is because the signal path in the image point 301 is configured inversely to the signal path in the image point 302. By contrast, the signal path in the image point 303 does not have a particularly high correlation with the signal paths in the image points 301, 302. During the course of the ICA, it was therefore possible to identify that the signal paths in the image points 301, 302 contribute to a common candidate correlation pattern.

Figure 5:
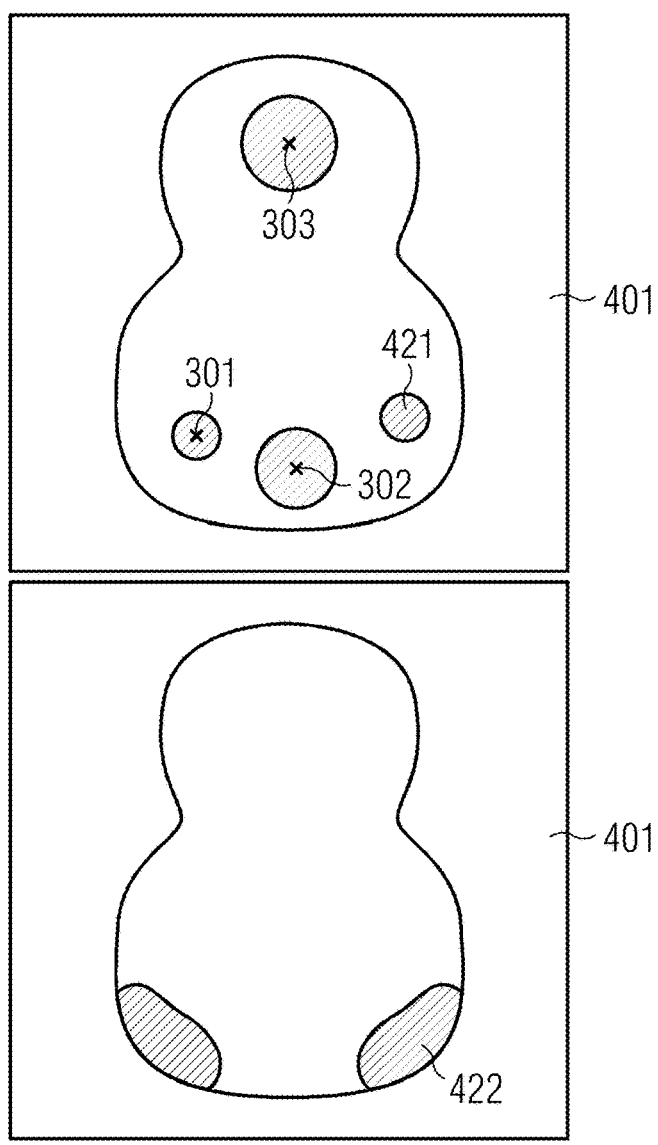
FIG. 5 schematically illustrates different candidate correlation patterns, which correspond to components of an ICA, which is carried out based on the image data of the brain, according to the invention.

FIG. 5 illustrates aspects in relation to the result of the ICA. FIG. 5 illustrates an image 401, which depicts a slice of the brain. FIG. 5 illustrates a transversal slice through the brain.

Shown overlaid on the image 401 are threshold value-filtered, spatially resolved intensities of different candidate correlation patterns 421, 422, which were identified by the ICA, (top and bottom in FIG. 5). The intensities can assume positive and negative values. The candidate correlation patterns 421, 422 correspond to different components of the ICA.

FIG. 5 illustrates two candidate correlation patterns 421, 422, which depict correlation patterns of actual neurophysical events. For example, the correlation pattern 421 is what is known as the default mode network, see Van Den Heuvel, Martijn P., and Hilleke E. Hulshoff Pol. "Exploring the brain network: a review on resting-state fMRI functional connectivity." European neuropsychopharmacology 20.8 (2010): 519-534, FIG. 2. The correlation pattern 422 is the extrastriate visual, see ebd.

The candidate correlation patterns 421, 422 show a high intensity (hatched areas in FIG. 5) in unconnected regions of the brain. It is possible for candidate correlation patterns to be identified, which have a significant intensity in overlapping regions of the brain (not shown in FIG. 5). Furthermore, FIG. 5 illustrates a scenario in which only two candidate correlation patterns 421, 422 are identified. In general it is possible, however, for a significantly larger number of candidate correlation patterns to be identified. In particular, it is possible for candidate correlation patterns to be identified, which do not correspond to correlation patterns of the neurophysical events but to false patterns, for example owing to noise (not shown in FIG. 5). Techniques will be described below, which enable correlation patterns of the neurophysical events to be separated from false patterns. For example, techniques of this kind can be carried out during the course of step 1004 in FIG. 2.

Such techniques can be carried out in particular in view of the fact that the ICA does not provide the candidate correlation patterns in a predetermined or deterministic order. In addition, the sign of the correlation patterns can vary non-deterministically. Furthermore, the number of candidate correlation patterns can depend on the number of observations. For this reason, a high number of false events can be obtained with a particularly high number of observations. Such boundary conditions of the algorithm underlying the ICA can be taken into account in the various examples described herein.

Figure 6:
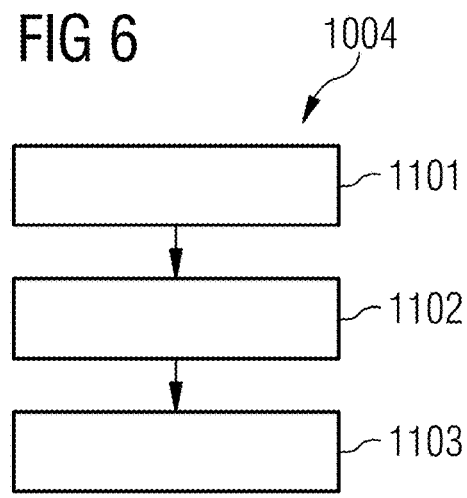
FIG. 6 is a flowchart of another example of the method according to the invention.

FIG. 6 is a flowchart of an exemplary method. For example, the method of FIG. 6 can be used for separating correlation patterns of the neurophysical events and false patterns on the basis of a large number of candidate correlation patterns, which were identified by an ICA. The method of FIG. 6 can be carried out for example in step 1004 of FIG. 2.

Figure 7:
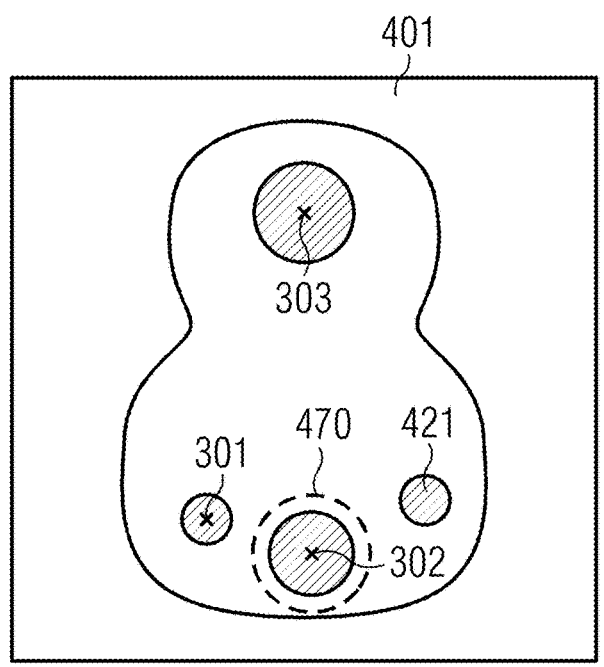
FIG. 7 schematically illustrates a section of the brain obtained according to the invention.

Firstly, a section of the brain is determined in step 1101 (cf. FIG. 7 where a section 470 of the brain in image 401 is highlighted by broken lines). In some examples it would be possible for the section 470 of the brain to be determined manually by a user. In other examples it would also be possible for anatomical regions of the brain to be segmented based on the image data 201-203 or reference image data, which is obtained for example by a reference MR scanning sequence. The section can then be determined based on segmenting. For example, segmenting could also comprise registering between the image data and reference image data in which the anatomical regions are annotated. For example, in other words, in step 1101 the section can be determined automatically. This can occur, for example, on registering of an anatomical atlas. For example, the user can choose the region relevant to him as section 470 from a list of known brain regions.

A one- or multi-dimensional value of a predefined metric is then determined in step 1102 for each candidate correlation pattern, which was identified previously by the ICA. The metric describes an intensity of the respective candidate correlation pattern in the section.

At least one candidate correlation pattern is then chosen in step 1103 on the basis of the determined values of the predefined metric for the various candidate correlation patterns. For example, those candidate correlation patterns could be chosen for step 1103, which have a particularly high or a particularly low intensity in the section. For example, a threshold value comparison can be carried out for this purpose. Chosen candidate correlation patterns can then be marked by a user for analysis. For example, it is possible to output chosen candidate correlation patterns via the user interface. For example, the user could obtain a sorted list of candidate correlation patterns, with the list being sorted according to the respectively determined values of the predefined metric.

A reduction in the sample space, which has to be analyzed by the user, can be achieved by such techniques. In particular, filtering can be achieved in relation to those candidate correlation patterns, which are relevant in relation to section 470—for example a ROI.

It should be noted in this connection that the ICA is carried out in a region of the brain, which includes the section and is greater than section 470, or in the entire brain. In other words, the choice of section does not affect implementation of the ICA. In contrast to reference implementations, the chosen section 470 is therefore not used as the basis for identification of the candidate correlation patterns. Instead, section 470 is only used following the ICA, namely to assist separation of false patterns from correlation patterns of the neurophysical events.

Appropriate choice of the metric can assist accurate separation between correlation patterns of the neurophysical events and false patterns. This can be promoted by consideration of the properties of the components extracted by the ICA when choosing the metric. For example, some techniques of the choice of metric are based on the knowledge that the ICA determines the candidate correlation patterns in a non-deterministic order and also with variable variance and variable sign. For this reason, in some examples it is possible for the metric to take into account a normalized variance of a component of the time series of image data, which corresponds to the respective candidate correlation patterns.

The metric can take into account an intensity of a component, integrated over section 470, of the time series 200 of image data 201-203, which corresponds to the respective candidate correlation patterns. For example, the metric can also take into account an integrated intensity of the normalized variance of a component as an integral over section 470. Section 470 can be defined for example two-dimensionally or three-dimensionally; and the integral can be defined two-dimensionally or three-dimensionally accordingly.

It is also possible for the metric to take into account a value of the intensity of a component of the time series 200 of image data 201-203, which corresponds to the respective candidate correlation pattern. This means that the sign of the intensity of a respective candidate correlation pattern can remain unconsidered. In this way, any signs, which are obtained for the different components by the ICA, can be compensated during determination of the intensity of the corresponding candidate correlation pattern in section 170. This is based on the knowledge that the sign of the intensity of the various candidate correlation patterns often has no physically relevant content.

In some examples the metric could take into account a difference between intensities of a component of the time series 200 of image data 201-203, which corresponds to the respective candidate correlation pattern, inside and outside of section 470. In this way, for example those candidate correlation patterns could be detected, which have a particularly uniform intensity inside and outside of section 470. Such candidate correlation patterns can for example be identified as false patterns because they are caused for example due to noise and are activated uniformly in the region of the brain or over extensive regions of the brain and are not limited to an anatomically relevant section 470. In this way, false patterns and correlation patterns of the neurophysical events can therefore be separated particularly efficiently.

Such techniques, as have been described in relation to the method of FIG. 6, therefore enable automatic detection of correlation patterns of the neurophysical events on the basis of a large number of candidate correlation patterns, which also include false patterns. In particular, detection of this kind can occur without error-prone and time-consuming manual definition of seed regions as an a priori limitation. A section can be taken into account following implementation of the ICA. The consistency of the detected correlation patterns of the neurophysical events can be greater compared to manually defined seed regions as an a priori limitation since the ICA does not generate any inconsistent "mixed regions" for example. It is therefore possible, for example, in reference techniques, which are based on a seed point as an a priori limitation, to define a seed region, which anatomically and in terms of connectivity does not form a single closed region. The quality of the extracted components suffers considerably as a result. Furthermore, the solution to this problem is not trivial since the result of the ICA is not yet available at the instant of determination of the seed regions. Drawbacks of this kind are avoided by the techniques described herein.

In the techniques described herein it is possible to determine the candidate correlation patterns completely automatically by means of the ICA. In a step that is independent thereof it is possible for a section to be specified by the user, which is particularly relevant to the current analysis. Only afterwards are these independent items of information linked to each other, so an imprecisely defined seed region as a priori information for the ICA does not affect the quality of the results or does not affect them significantly.

Figure 8:
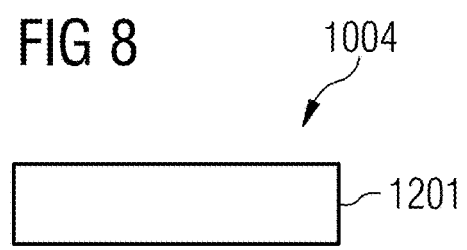
FIG. 8 is a flowchart of an embodiment of the invention.

FIG. 8 is a flowchart of an exemplary method. In particular, FIG. 8 illustrates techniques in relation to the separation of correlation patterns of the neurophysical events from false patterns. For example, the method of FIG. 8 can be carried out during the course of step 1004 in FIG. 2.

In step 1201 a computer-implemented classifier is applied to the large number of candidate correlation patterns, which were identified during the course of the ICA. The classifier is adapted to achieve a separation of the false patterns and correlation patterns of the large number of neurophysical events.

Effects of this kind are based on the knowledge that often false patterns can have a characteristic position space profile of the intensity. For example, false patterns can have a characteristic position space profile owing to movement—for example caused by physiological effects such as breathing—or owing to blood flow—for example caused by physiological effects such as heartbeat. For example, the position space profile of false patterns can have a particularly high intensity at the periphery of the brain owing to movement because opposing sides of the brain move in a correlated manner. On the basis of this knowledge it can be particularly easily possible to detect false patterns by means of the computer-implemented classifier.

For example, an ANN could be used as a classifier. An exemplary ANN is a CNN. Corresponding techniques are basically known to the person skilled in the art from: Krizhevsky, Alex, Ilya Sutskever, and Geoffrey E. Hinton. "ImageNet Classification with Deep Convolutional Neural Networks." Advances in neural information processing systems. 2012 and Lawrence, Steve, et al. "Face recognition: A convolutional neural-network approach." IEEE transactions on neural networks 8.1 (1997): 98-113. With a CNN, spatially limited three-dimensional regions are convoluted with three-dimensional kernels. This means that there is no complete linking of a neuron of a slice to all neurons of a preceding slice. A translation invariance is achieved in that each kernel is convoluted with all possible sensitive regions. The CNN can also support a plurality of hidden layers. Depending on the number of layers used, a different number of features can be detected in the input data, in other words, the image data provided by the ICA, which depict the candidate correlation patterns. At the same time, the number of parameters is reduced. Pooling slices can also be used, which consolidate the results of preceding slices. Completely linked slices can also be used, typically close to the output layer.

An ANN can be trained on the basis of generally known techniques. For example, the back propagation algorithm can be used, see Rumelhart, David E., Geoffrey E. Hinton, and Ronald J. Williams. "Learning representations by back-propagating errors." Cognitive modeling 5.3 (1988): 1. A quantity of known training pairs of components of an ICA with respect to categories is typically required for this. The categories are for example manually assigned by an experienced user, for instance. The result of training then exists in a quantity of edge weights for the corresponding ANN, which characterize the respective weighting of the data during the passage through the ANN from the input layer through to the output layer. Once the ANN has been trained, typically no further interaction is required for classification of the components of the ICA or the candidate correlation patterns. The quantity of components of the ICA can then be iteratively classified by the ANN.

Different categories, which are acquired by the classifier, are conceivable in different examples. For example, the different categories can be learned by appropriate training of the classifier. The classifier could for instance be adapted for the separation between correlation patterns of different types of spontaneous neurophysical events. Examples of correlation patterns of spontaneous neurophysical events comprise for example "Default Mode Network", "Attention Network", etc. The correlation patterns of different types of spontaneous neurophysical events are described for example in: Greicius, Michael D., et al. "Functional connectivity in the resting brain: a network analysis of the default mode hypothesis." Proceedings of the National Academy of Sciences 100.1 (2003): 253-258.

By the techniques described herein it is therefore possible to carry out an automatic selection of relevant correlation patterns of neurophysical events on the basis of a computer-implemented classification of components of an ICA, which correspond to candidate correlation patterns. A manual selection is omitted. User interaction in connection with the rsfMRI is simplified considerably as a result.

The various techniques described herein can be carried out for example by the processor 161 of the MR system 100. It would also be possible, to use cloud computing. For example, the candidate correlation patterns could be transferred to a server and the server could then be adapted for the separation between the correlation patterns of the neurophysical events and false patterns.

Of course, the features of the above-described embodiments and aspects of the invention can be combined with each other. In particular, the features can be used not just in the described combinations, but also in other combinations or alone, without the departing from the field of the invention.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for magnetic resonance (MR) imaging, comprising:
   operating an MR data acquisition scanner in order to acquire a time series of raw MR data that represents a plurality of spatially-resolved neurophysical events in the brain of a subject;
   in a computer, reconstructing image data from said raw MR data depicting the brain with said spatially-resolved neurophysical events therein;
   in said computer, performing an independent component analysis (ICA) in order to identify a plurality of candidate correlation patterns among said plurality of neurophysical events, said plurality of candidate correlation patterns comprising actual correlation patterns of said plurality of neurophysical events and false patterns;
   in said computer, determining a section of the brain of the subject in the reconstructed image data;
   in said computer, for each candidate correlation pattern in said plurality of candidate correlation patterns, determining a corresponding value of a predetermined metric that indicates an intensity of the respective candidate correlation pattern in the determined section of the brain, wherein said predetermined metric represents a value of an intensity and a normalized variance of a component of said time series in the reconstructed image data, which corresponds to the respective candidate correlation pattern;
   in said computer, selecting at least one candidate correlation pattern from said plurality of candidate correlation patterns dependent on the value of the predetermined metric thereof; and
   presenting the at least one selected candidate correlation pattern at a display screen in communication with said computer for analysis by a user, marked as the selected at least one candidate correlation pattern.

2. The method as claimed in claim 1 comprising employing, as said predetermined metric, a metric that represents an intensity, integrated over said determined section of the brain of the subject, of a component of the time series of the reconstructed image data, which corresponds to the respective candidate correlation pattern.

3. The method as claimed in claim 1 comprising employing, as said predetermined metric, a metric that represents a difference between intensities of a component of the time series of the reconstructed image data, which corresponds to the respective candidate correlation pattern inside and outside of the determined section of the brain of the subject.

4. The method as claimed in claim 1 comprising determining said section of the brain of the subject by segmenting anatomical regions of the brain based on at least one of said image data or reference image data, and determining said section of the brain from said segmenting.

5. The method as claimed in claim 1 comprising conducting said ICA in a region of the brain that includes said determined section and that is larger than said predetermined section.

6. The method as claimed in claim 1 comprising conducting said ICA over an entirety of the brain of the subject.

7. The method as claimed in claim 1 wherein the selecting said at least one candidate correlation pattern from said plurality of candidate correlation patterns is based on a threshold value comparison.

8. A non-transitory, computer-readable data storage medium encoded with programming instructions, said storage medium being loaded into a computer system of a magnetic resonance (MR) apparatus comprising an MR data acquisition scanner, said programming instructions causing said computer system to:
   operate said MR data acquisition scanner in order to acquire a time series of raw MR data that represents a plurality of spatially-resolved neurophysical events in the brain of a subject;
   reconstruct image data from said raw MR data depicting the brain with said spatially-resolved neurophysical events therein;
   perform an independent component analysis (ICA) in order to identify a plurality of candidate correlation patterns among said plurality of neurophysical events, said plurality of candidate correlation patterns comprising actual correlation patterns of said plurality of neurophysical events and false patterns;
   determine a section of the brain of the subject in the reconstructed image data;
   for each candidate correlation pattern in said plurality of candidate correlation patterns, determine a corresponding value of a predetermined metric that indicates an intensity of the respective candidate correlation pattern in the determined section of the brain, wherein said predetermined metric represents a difference between intensities and a normalized variance of a component of said time series in the reconstructed image data, which corresponds to the respective candidate correlation pattern inside and outside of the determined section of the brain of the subject;

select at least one candidate correlation pattern from said plurality of candidate correlation patterns dependent on the value of the predetermined metric thereof; and present the at least one selected candidate correlation pattern at a display screen in communication with said computer for analysis by a user, marked as the selected at least one candidate correlation pattern.

9. The non-transitory, computer-readable data storage medium as claimed in claim 8 wherein the selecting said at least one candidate correlation pattern from said plurality of candidate correlation patterns is based on a threshold value comparison.

10. A magnetic resonance (MR) apparatus comprising:

an MR data acquisition scanner;

a computer configured to operate an MR data acquisition scanner in order to acquire a time series of raw MR data that represents a plurality of spatially-resolved neurophysical events in the brain of a subject;

said computer being configured to reconstruct image data from said raw MR data depicting the brain with said spatially-resolved neurophysical events therein;

said computer being configured to perform an independent component analysis (ICA) in order to identify a plurality of candidate correlation patterns among said plurality of neurophysical events, said plurality of candidate correlation patterns comprising actual correlation patterns of said plurality of neurophysical events and false patterns;

said computer being configured to determine a section of the brain of the subject in the reconstructed image data;

said computer, for each candidate correlation pattern in said plurality of candidate correlation patterns, being configured to determine a corresponding value of a predetermined metric that indicates an intensity of the respective candidate correlation pattern in the determined section of the brain, wherein said predetermined metric represents an intensity, integrated over said determined section of the brain of the subject, and a normalized variance of a component of said time series in the reconstructed image data, which corresponds to the respective candidate correlation pattern;

said computer being configured to select at least one candidate correlation pattern from said plurality of candidate correlation patterns dependent on the value of the predetermined metric thereof;

a display screen in communication with said computer; and said computer being configured to present the at least one selected candidate correlation pattern at said display screen in communication with said computer for analysis by a user, marked as the selected at least one candidate correlation pattern.

11. The magnetic resonance (MR) apparatus as claimed in claim 10 wherein the selecting said at least one candidate correlation pattern from said plurality of candidate correlation patterns is based on a threshold value comparison.

* * * * *